(12) United States Patent
Skinner

(10) Patent No.: US 6,516,232 B2
(45) Date of Patent: Feb. 4, 2003

(54) RING ELECTRODE WITH POROUS MEMBER

(75) Inventor: Dwight Skinner, St. Anthony, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 5 days.

(21) Appl. No.: 09/907,540

(22) Filed: Jul. 17, 2001

(65) Prior Publication Data

US 2002/0042643 A1 Apr. 11, 2002

Related U.S. Application Data

(63) Continuation of application No. 09/352,557, filed on Jul. 13, 1999, now Pat. No. 6,263,250.

(51) Int. Cl.[7] .................................................. A61N 1/05
(52) U.S. Cl. ........................................ 607/122; 29/825
(58) Field of Search ................................ 607/119, 121, 607/122, 123, 126, 129; 600/373–375; 606/41; 29/825, 829, 875; 174/68.1; 264/104

(56) References Cited

U.S. PATENT DOCUMENTS

| 4,156,429 A | 5/1979 | Amundson ................... 128/419 |
| 4,587,975 A | 5/1986 | Salo et al. ................... 128/693 |
| 4,762,136 A | 8/1988 | Baker, Jr. ................... 128/786 |
| 4,922,607 A | 5/1990 | Doan et al. ................... 29/879 |
| 4,944,088 A | 7/1990 | Doan et al. ................... 29/858 |
| 4,967,755 A | 11/1990 | Pohndorf et al. ........... 128/675 |
| 5,007,435 A | 4/1991 | Doan et al. ................... 128/784 |
| 5,074,313 A | 12/1991 | Dahl et al. ................... 128/784 |
| 5,143,090 A | 9/1992 | Dutcher et al. ............. 128/785 |
| 5,330,522 A | 7/1994 | Kreyenhagen ............... 607/122 |
| 5,368,564 A | 11/1994 | Savage ......................... 604/95 |
| 5,464,404 A | 11/1995 | Abela et al. ................... 606/15 |
| 5,476,502 A | 12/1995 | Rubin ......................... 607/127 |
| 5,507,725 A | 4/1996 | Savage et al. ................. 604/95 |
| 5,534,022 A | 7/1996 | Hoffmann et al. .......... 607/122 |
| 5,545,205 A | 8/1996 | Schulte et al. .............. 607/123 |
| 5,632,770 A | 5/1997 | Schaldach ................... 607/122 |
| 5,643,197 A | 7/1997 | Brucker et al. ............... 604/20 |
| 5,645,580 A | 7/1997 | Moaddeb et al. ........... 607/122 |
| 5,683,443 A | 11/1997 | Munshi et al. .............. 607/121 |
| RE35,924 E | 10/1998 | Winkler ...................... 600/373 |
| 5,824,016 A | 10/1998 | Ekwall ........................... 607/9 |
| 5,899,929 A | 5/1999 | Thompson et al. ........... 607/28 |
| 5,935,102 A | 8/1999 | Bowden et al. ............... 604/95 |
| 5,935,160 A | 8/1999 | Auricchio et al. .......... 607/122 |
| 5,954,649 A | 9/1999 | Chia et al. ................... 600/424 |
| 6,029,091 A | 2/2000 | de la Rama et al. ........ 607/102 |
| 6,263,250 B1 * | 7/2001 | Skinner ....................... 600/325 |

FOREIGN PATENT DOCUMENTS

| EP | 0813885 | 6/1997 | ............ A61N/1/05 |
| EP | 0813886 | 12/1997 | ............ A61N/1/05 |
| GB | 2065478 | 12/1980 | ............ A61N/1/04 |

* cited by examiner

Primary Examiner—Jeffrey R. Jastrzab
(74) Attorney, Agent, or Firm—Schwegman, Lundberg, Woessner & Kluth, P.A.

(57) ABSTRACT

A lead assembly having a ring electrode is adapted for implant and for connection to a system for monitoring or stimulating cardiac activity. The lead assembly includes a first porous member disposed around the ring electrode at the distal end of the lead assembly, which can be used as a sensing or pacing interface with the cardiac tissue. In addition, a second porous member is disposed over the first porous member and is electrically coupled with the ring electrode.

25 Claims, 4 Drawing Sheets

RING ELECTRODE WITH POROUS MEMBER

CROSS REFERENCE TO RELATED APPLICATIONS

This application is a continuation of U.S. patent application No. 09/352,557, filed on Jul. 13, 1999, now U.S. Pat. No. 6,263,250 the specification of which is incorporated herein by reference.

TECHNICAL FIELD

The present invention relates generally to leads for conducting electrical signals to and from the heart. More particularly, it pertains to a ring electrode for pacing electrical signals from the heart.

BACKGROUND

Leads implanted in or about the heart have been used to reverse certain life threatening arrhythmias, or to stimulate contraction of the heart. Electrical energy is applied to the heart via the leads to return the heart to normal rhythm. Leads have also been used to sense in the atrium or ventricle of the heart and to deliver pacing pulses to the atrium or ventricle. Technically, the pacemaker or the automatic implantable cardioverter defibrillator (AICD) receives signals from the lead and interprets them. In response to these signals the pacemaker can pace or not pace. The AICD can pace, not pace or shock, and not shock. In response to a sensed bradycardia or tachycardia condition, a pulse generator produces pacing or defibrillation pulses to correct the condition. The same lead used to sense the condition is sometimes also used in the process of delivering a corrective pulse or signal from the pulse generator of the pacemaker.

Cardiac pacing may be performed by the transvenous method or by leads implanted directly onto the ventricular epicardium. Most commonly, permanent transvenous pacing is performed using a lead positioned within one or more chambers of the heart. The lead may also be positioned in both chambers, depending on the lead, as when a lead passes through the atrium to the ventricle. sense electrodes may be positioned within the atrium or the ventricle of the heart. For pacing applications, the lead may be positioned in cardiac veins or arteries.

Positioning an electrode disposed on a distal end of a lead within a vein or artery presents additional challenges in maintaining the lead in a fixed position since the distal end of the lead does not abut a surface. These challenges also may result in poor pacing and sensing capabilities of the electrode.

Therefore, there is a need for a lead having an electrode for positioning within cardiac veins, or arteries that allows for fixation therein. In addition, what is needed is a lead which provides desirable pacing and sensing properties.

SUMMARY

A body-implantable lead assembly includes a lead, one end being adapted to be connected to electrical supply for providing or receiving electrical pulses. The lead extends to a distal end which is adapted to be connected to tissue of a living body. The lead also has a sheath of material inert to body materials and fluids and at least one conductor extending through the lead body.

The distal end of the lead assembly is adapted for implantation proximate to or within the heart while connected with a system for monitoring or stimulating cardiac activity. In addition, the distal end of the lead assembly is implanted in cardiac veins or arteries, depending on the application. The distal end includes a ring electrode electrically coupled with a first porous member electrically coupled with the ring electrode. A conductor coil is disposed within the lead body and is electrically coupled with the ring electrode.

In one embodiment, the ring electrode includes a cut out, and the first porous member is disposed in the cut out. The first porous member is electrically active, and paces and/or senses the tissue once it is implanted. In addition, the surface area of the first porous member is changed to control electrically properties of the lead assembly. The first porous member is formed of a material which is inert to a living body.

The first porous member, in another embodiment, includes a mesh screen. The mesh screen is formed of various materials, including, but not limited to, platinum iridium, iridium oxide, titanium nitride, titanium oxide, diamond, tantalum. In another embodiment, the first porous member is sputter coated on the ring electrode with liquid metal. In yet another embodiment, the first porous member is formed by etching the ring electrode with acid. The first porous member, in one embodiment, is formed by laser scribing the ring electrode. In another embodiment, the first porous member is formed by particle blasting the ring electrode. In yet another embodiment, the first porous member is formed by chemical vapor deposition of the ring electrode. The first porous member, in another embodiment, is formed by coating the ring electrode with diamond.

In another embodiment, a ring electrode is electrically coupled with the conductor and a first porous member electrically coupled with the ring electrode. A second porous member is disposed over the first porous member, and each is electrically coupled with the ring electrode. The second porous member is bonded with the ring electrode, for instance, by sintering or welding. The first porous member and the second porous member are electrically active, and can pace and/or sense the tissue once it is implanted.

The above-described lead assembly provides several benefits including increased sensing and pacing properties. Furthermore, the first and/or second porous members will assist in retaining the electrode assembly in a desired location due to the tissue ingrowth.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1:
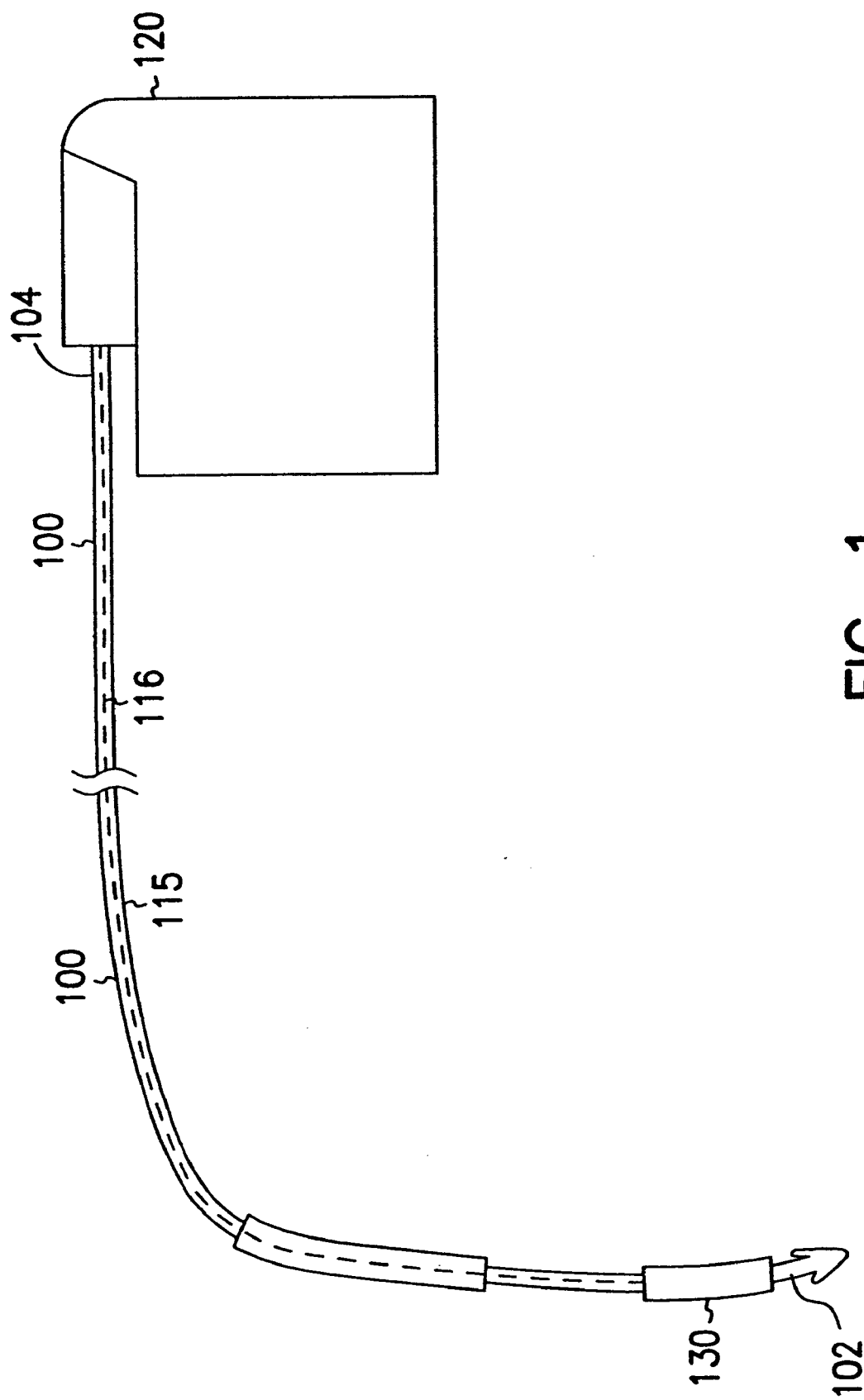
FIG. 1 is an elevational view illustrating a lead assembly constructed in accordance with one embodiment of the assembly.

FIG. 1 illustrates a lead 100 for delivering electrical pulses to stimulate a heart and/or for receiving electrical pulses to monitor the heart. The lead 100 has a distal end 102 adapted for implant within a body, for instance within a vein, and a proximal end 104. The proximal end 104 has a connector terminal which electrically connects the various electrodes and conductors within the lead 100 to a pulse generator 120 and signal sensor. The terminal connector provides for the electrical connection between the lead 100 and the pulse generator 120. The pulse generator 120 contains electronics to sense various electrical signals of the heart and also to produce current pulses for delivery to the heart.

The lead 100 includes a lead body 115, an elongate conductor 116 contained within the lead body 115, and at least one electrode assembly 130. The lead body 115 is covered by a biocompatible insulating material. Silicone rubber or other insulating material is used for covering the lead body 115. In one embodiment, the electrode assembly 130 is disposed proximate to the distal end 102 of the lead 100. In another embodiment, the electrode assembly 130 is disposed between the distal end 102 and the proximal end 104 of the lead 100.

The conductor 116 comprises a coil, which has been shown to be capable of withstanding constant, rapidly repeated flexing for years. The coiled construction is wound relatively tightly providing a maximum number of conductor turns per unit length, which allows for strain distribution. The spirally coiled spring construction of the conductor also permits a substantial degree of elongation, within the elastic limits of the material, as well as distribution along the conductor of flexing stresses which otherwise might be concentrated at a particular point.

Figure 2A:
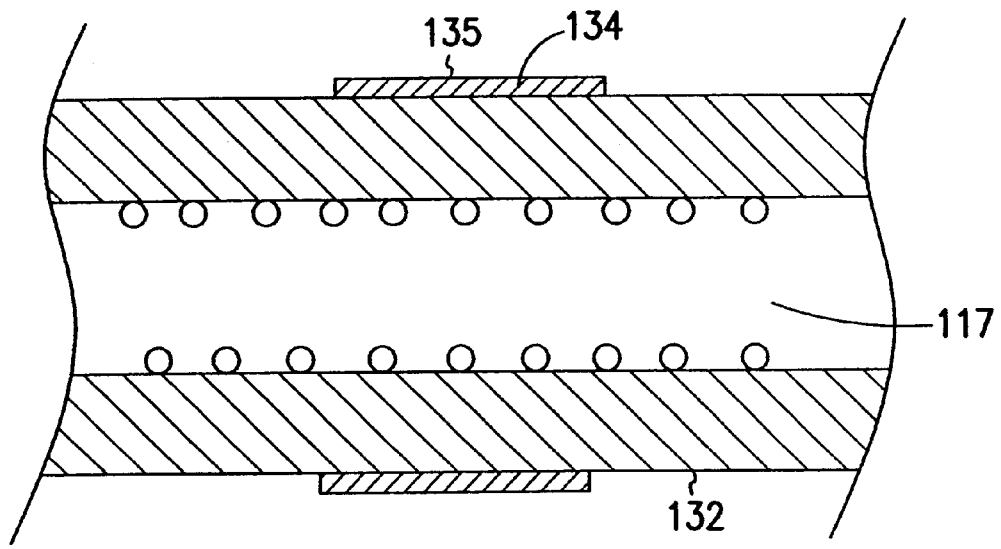
FIG. 2A is cross-section view of a distal end of a lead assembly constructed in accordance with one embodiment of the assembly.
Figure 2B:
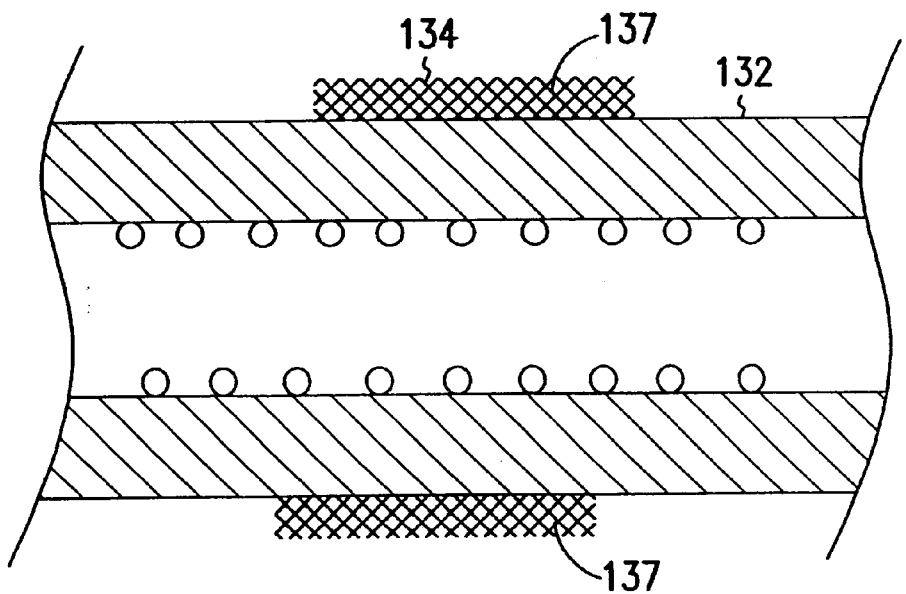
FIG. 2B is cross-section view of a distal end of a lead assembly constructed in accordance with one embodiment of the assembly.
Figure 2C:
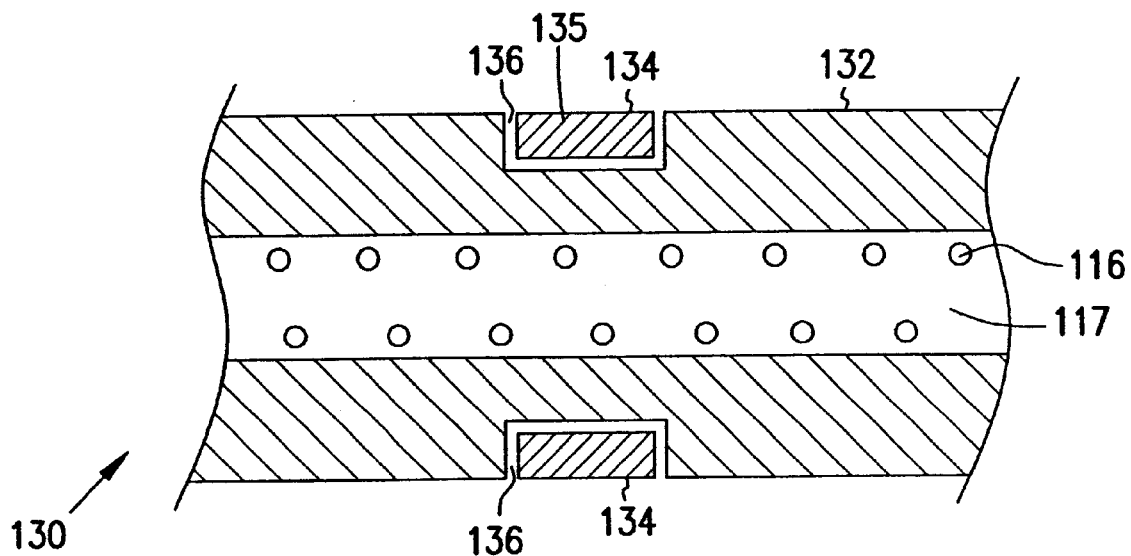
FIG. 2C is cross-section view of a distal end of a lead assembly constructed in accordance with one embodiment of the assembly.
Figure 2D:
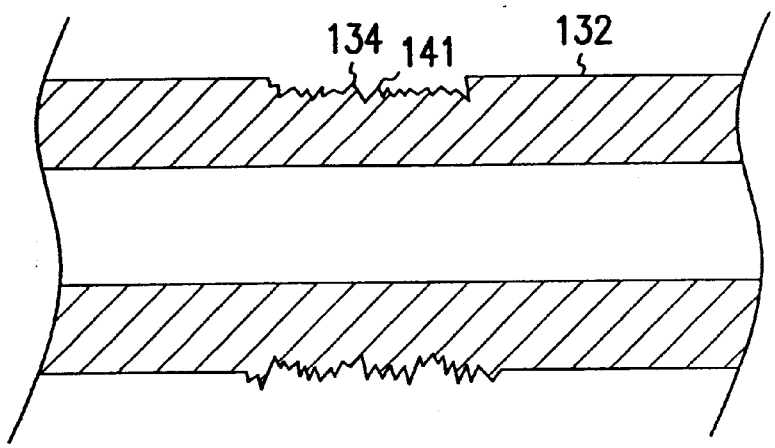
FIG. 2D is cross-section view of a distal end of a lead assembly constructed in accordance with one embodiment of the assembly.
Figure 3:
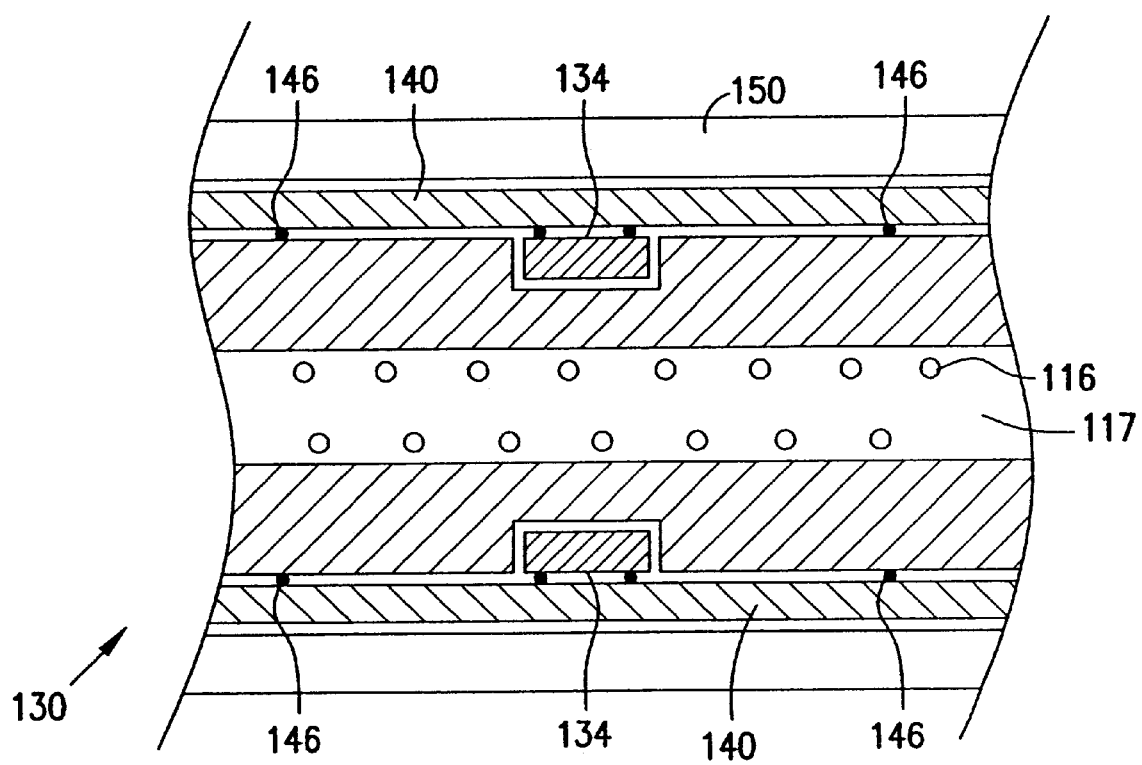
FIG. 3 is cross-section view of a distal end of a lead assembly constructed in accordance with another embodiment of the assembly.

The elongate conductor 116 defines a lumen 117 therein, as shown in FIGS. 2 and 3, and thereby is adapted to receive a stiffening stylet that extends through the length of the lead 100. Referring again to FIG. 1, the stylet stiffens the lead 100, and can be manipulated to introduce an appropriate curvature to the lead 100. The manipulation of the stylet facilitates the insertion of the lead 100 into and through a vein and through an intracardiac valve to advance the distal end 102 of the lead 100 into, for example, the right ventricle of the heart. A stylet knob is coupled with the stylet for rotating the stylet, advancing the conductor into tissue of the heart, and for manipulating the lead 100.

The electrode assembly 130 is adapted to be coupled with tissue of a patient, for example, within a heart, or within a vein or artery 150 (FIG. 3). Referring to FIG. 2A, the electrode assembly 130, includes a ring electrode 132. The ring electrode 132 includes a first porous member 134. In one embodiment, the first porous member 134 is fully disposed over the ring electrode 132. Alternatively, the first porous member 134 is partially disposed over the ring electrode 132, or the first porous member 134 is disposed completely around the circumference of the ring electrode 132. In one embodiment, the first porous member 134 comprises a mesh 135 made of platinum wire, where the mesh 135 is disposed over the ring electrode 132.

The first porous member 134 is formed by creating a texture or increasing the surface area directly on the ring electrode 132. For instance, a conductive material 137 is coated on the ring electrode 132, as shown in FIG. 2B. In another embodiment, as shown in FIG. 2D, a layer of material from the ring electrode 132 is removed, exposing a textured surface 141 to form the first porous member 134. Other processes for forming the first porous member 134 include liquid metal coating, electrode burning, laser scribing, acid etching, mechanical abrasion, particle blasting, thermal spray coating, chemical vapor deposition, plasma etching, diamond coating, and powder metallurgy such as casting or forming processes. Using these processes allows for the surface area of the ring electrode 132 to increase, thereby increasing the sensing and pacing abilities of the ring electrode 132.

The first porous member 134 is of a porous construction, made of electrically conductive, corrosion resistant material. One example of a suitable material for the first porous member 134 is platinum iridium. Other suitable materials include diamond, iridium oxide, titanium nitride, titanium oxide, platinum, titanium, and tantalum. Using a first porous member 134 having a porous construction allows for fibrotic ingrowth, which provides for a further anchoring the electrode and also increases the sensing capability of the lead 100 by increasing the surface area in contact with the cardiac tissue. The surface area of the first porous member 134 can be changed to control electrically properties of the lead assembly.

The first porous member 134 is disposed, in one embodiment, within a cut out 136 disposed within the ring electrode 132, as shown in FIG. 2C. The cut out 136 is not limited to any particular shape. For instance, the cut out 136 comprises in one embodiment one or more cuts to the outer circumference of the ring electrode 132. In another embodiment, the cut out 136 comprises an annular cut out. The first porous member 134, in another embodiment, is physically and/or electrically attached to the ring electrode 132, such as by welding or soldering. Other methods for attaching the first porous member 134 to the ring electrode 132 include, but are not limited to metal bonding, diffusion bonding, or an interference fit between the first porous member 134 and the cut out 136. Other attachment methods may be used without departing from the scope of that described herein.

In another embodiment, illustrated in FIG. 3, the electrode assembly 130 includes a ring electrode 132, which is known to those skilled in the art. Disposed over the ring electrode 132 is a first porous member 134, as discussed above. The first porous member 134 is disposed partially over the ring electrode 132. Alternatively, the first porous member 134 is disposed completely around the circumference of the ring electrode 132. The electrode assembly 130 further includes a second porous member 140, which is disposed over the first porous member 134. The second porous member 140 is wider than the first porous member 134. The second porous member 140 is physically and/or electrically attached to the ring electrode 132 at 146, such as by welding, applying conductive adhesive, or crimping. In another embodiment, the second porous member 140 is bonded to the first porous member 134 and/or the ring electrode 132 by sintering.

In one embodiment, the second porous member 140 comprises a mesh formed of wire, such as platinum. In another embodiment, the second porous member 140 is formed by creating a texture or increasing the surface area directly on the ring electrode 132 and the first porous member 134. For instance, a conductive material is coated on the ring electrode 132 and the first porous member 134. Other processes for forming the second porous member 140 having an increased texture or surface area include, but are not limited to, liquid metal coating, electrode burning, laser scribing, acid etching, mechanical abrasion, particle blasting, thermal spray coating, chemical vapor deposition, plasma etching, diamond coating, and powder metallurgy such as casting or forming processes. Using these processes allows for the surface area of the ring electrode 132 to increase, thereby increasing the sensing and pacing abilities of the ring electrode 132.

The second porous member 140 is of a porous construction, made of electrically conductive, corrosion resistant material. One example of a suitable material for the second porous member 140 is platinum iridium. Other suitable materials include, but are not limited to diamond, iridium oxide, titanium nitride, titanium oxide, platinum, titanium, and tantalum. A second porous member 140 having a porous construction allows for fibrotic ingrowth, which provides for a further anchoring the electrode within the heart or within a vein 150 and also increases the sensing capability of the lead 100 by increasing the surface area in contact with the cardiac tissue.

The above-described lead assembly provides several benefits including increased sensing and pacing properties. Furthermore, the first and/or second porous members will assist in retaining the electrode assembly in a desired location due to the tissue ingrowth. The lead assembly is also beneficial in applications where the ring electrode is disposed in a larger vein or artery where it is otherwise difficult to position and/or maintain the ring electrode against the wall of the surrounding tissue.

It is to be understood that the above description is intended to be illustrative, and not restrictive. Although the use of the lead has been described for use in a cardiac pacing system, the lead could be applied to other types of body stimulating systems. Many other embodiments and applications will be apparent to those of skill in the art upon reviewing the above description.

What is claimed is:

1. A method for forming a lead assembly comprising:
   disposing a conductor within a lead body;
   coupling a ring electrode with the conductor, the ring electrode having a surface area;
   increasing the surface area of the ring electrode and forming a first porous member on the ring electrode;
   disposing a second porous member formed of a conductive material directly over a circumference of the ring electrode and over the increased surface area of the ring electrode, where the second porous member is wider than the first porous member; and
   mechanically coupling the second porous member with the lead body and electrically coupling the second porous member with the ring electrode.

2. The method as recited in claim 1, further comprising sputter coating the first porous member on the ring electrode.

3. The method as recited in claim 1, further comprising etching the ring electrode with acid.

4. The method as recited in claim 1, further comprising laser scribing the ring electrode.

5. The method as recited in claim 1, further comprising particle blasting the ring electrode.

6. The method as recited in claim 1, further comprising depositing the first porous member by chemical vapor deposition of the ring electrode.

7. The method as recited in claim 1, further comprising coating diamond on the ring electrode.

8. A method for forming a lead assembly comprising:
   disposing a conductor within a lead body;
   electrically coupling an electrode assembly with the conductor, the electrode assembly including a ring electrode having a surface area;
   coupling the ring electrode around a circumference of the lead body;
   disposing a first mesh screen around a circumference of the ring electrode to form a first porous member;
   coating a second porous member formed of a conductive material directly over the first mesh screen and over the circumference of the ring electrode; and
   mechanically coupling the second porous member with the lead body and electrically coupling the second porous member with the ring electrode.

9. The method as recited in claim 8, further comprising forming a cut out in the ring electrode, and disposing the first mesh screen within the cut out.

10. The method as recited in claim 8, wherein the second porous member is coated wider than the first mesh screen.

11. The method as recited in claim 8, wherein coating the second porous member comprises laser scribing the second porous member on to the first porous member.

12. The method as recited in claim 8, wherein coating the second porous member comprises particle blasting the second porous member on to the first porous member.

13. The method as recited in claim 8, wherein coating the second porous member comprises thermal spray coating the second porous member on to the first porous member.

14. The method as recited in claim 8, wherein coating the second porous member comprises diamond coating the second porous member on to the first porous member.

15. The method as recited in claim 8, wherein coating the second porous member comprises depositing by chemical vapor deposition the second porous member on to the first porous member.

16. The method as recited in claim 8, wherein coating the second porous member comprises acid etching the second porous member on to the first porous member.

17. A method for forming a lead assembly comprising:
   disposing a conductor within a lead body;
   electrically coupling an electrode assembly with the conductor, the electrode assembly including a ring electrode having a surface area;
   coupling the ring electrode around a circumference of the lead body;
   forming an annular cut out around a circumference of the ring electrode;
   disposing a first porous member around the ring electrode within the annular cut out of the ring electrode;
   coating a second porous member formed of a conductive material directly over the ring electrode and over the circumference of the ring electrode, where the coating is wider than the first porous member; and electrically coupling the second porous member with the ring electrode.

18. The method as recited in claim 17, further comprising forming a cut out in the ring electrode, and disposing the first mesh screen within the cut out.

19. The method as recited in claim 17, wherein the second porous member is coated wider than the first mesh screen.

20. The method as recited in claim 17, wherein coating the second porous member comprises laser scribing the second porous member on to the first porous member.

21. The method as recited in claim 17, wherein coating the second porous member comprises particle blasting the second porous member on to the first porous member.

22. The method as recited in claim 17, wherein coating the second porous member comprises thermal spray coating the second porous member on to the first porous member.

23. The method as recited in claim 17, wherein coating the second porous member comprises diamond coating the second porous member on to the first porous member.

24. The method as recited in claim 17, wherein coating the second porous member comprises depositing by chemical vapor deposition the second porous member on to the first porous member.

25. The method as recited in claim 17, wherein coating the second porous member comprises acid etching the second porous member on to the first porous member.

* * * * *